United States Patent [19]
Grentzmann et al.

[11] Patent Number: 6,143,502
[45] Date of Patent: Nov. 7, 2000

[54] DUAL-LUCIFERASE REPORTER SYSTEM

[75] Inventors: Guido Grentzmann; Raymond F. Gesteland, both of Salt Lake City, Utah; John F. Atkins, Verrières le Buisson, France

[73] Assignee: University of Utah Research Foundation, Salt Lake City, Utah

[21] Appl. No.: 09/282,996

[22] Filed: Mar. 31, 1999

[51] Int. Cl.⁷ .............................. C12Q 1/68; C12Q 1/66; C12N 15/79
[52] U.S. Cl. .................. 435/6; 435/8; 435/320.1
[58] Field of Search .................. 435/320.1, 6, 29, 435/8, 252.3, 325, 410; 536/23.1, 23.2

[56] References Cited

U.S. PATENT DOCUMENTS 5,744,320  4/1998  Sherf et al. ..................... 435/8

OTHER PUBLICATIONS

Stahl, Guillaume et al. "Versatile vectors to study recoding: conservation of rules between yeast and mammalian cells" Nucleic Acids Research vol. 23 No. 9 pp. 1557–1560, 1995.
Sambrook, J. et al "Molecular Cloning: A Laboratory Manual" 2d ed. Cold Spring Harbor Laboratory Press, Cold Spring Harobor NY Section 1.7–1.8, 1989.

*Primary Examiner*—Terry McKelvey
*Assistant Examiner*—Gerald George Leffers, Jr.
*Attorney, Agent, or Firm*—Clayton, Howarth & Cannon, P.C.

[57] ABSTRACT

Plasmids and methods of use for assaying translational recoding are disclosed. The plasmids contain a constitutively expressed renilla (*Renilla reniformis*; sea pansy) luciferase gene, a polylinker for insertion of a selected DNA segment, and an out-of-frame firefly luciferase gene. Recoding is determined by monitoring luminescence of the firefly luciferase normalized to the luminescence of the renilla luciferase.

26 Claims, 2 Drawing Sheets

DUAL-LUCIFERASE REPORTER SYSTEM

STATEMENT REGARDING FEDERALLY SPONSORED RESEARCH OR DEVELOPMENT

This invention was made with government support under Grant No. RO1-GM48152-05 awarded by the National Institutes of Health. The government has certain rights in the invention.

BACKGROUND OF THE INVENTION

This invention relates to a translational reporter system. More particularly, the invention relates to a reporter system and method of use thereof for quantification of translational recoding, reinitiation, and internal initiation in eukaryotes in vivo and in vitro.

There are a number of cases where a single messenger RNA (mRNA) is translated into more than one protein by "recoding." "Recoding" has been defined as a phenomenon where the rules for translation decoding are temporarily altered through specific sites and signals built into the mRNA sequences (I. Brierly, Ribosomal Frameshifting on Viral RNAs, 76 J. Gen. Virol. 1885–1892 (1995); R. F. Gesteland & J. Atkins, Recoding: Dynamic Reprogramming of Translation, 65 Annu. Rev. Biochem. 741–768 (1996)). In some cases of recoding, special signals are far distant 3' on the message (M. J. Berry et al., Functional Characterization of the Eukaryotic SECIS Elements which Direct Selenocysteine Insertion at UGA Codons, 12 EMBO J. 3315–3322 (1993); W. A. Miller et al., New Punctuation for the Genetic Code: Luteovirus Gene Expression, 8 Sem. Virol. 3–13 (1997)). For studying the great majority of known cases of recoding, where the signals are close to the recoding site, it is helpful to measure the synthesis of two proteins. This has typically been done by monitoring radioactive proteins separated by SDS gel electrophoresis or by some combination with enzyme assays. These studies would be aided by a convenient and rapid assay suitable for both in vitro and in vivo screening of products.

In mammalian cells, three kinds of recoding have been described. First, redefinition of stop codons to sense codons (i.e., readthrough) allows synthesis of selenocysteine-containing proteins (A. Bock et al., Selenoprotein Synthesis: An Expansion of the Genetic Code, 16 Trends Biochem. Sci. 463–467 (1991); S. C. Low & M. J. Berry, Knowing When Not to Stop: Selenocysteine Incorporation in Eukaryotes, 21 Trends Biochem. Sci. 203–208 (1996)) and synthesis of elongated proteins in many RNA viruses, such as Moloney murine leukemia virus (MuLV) (Y. Yoshinaka et al., Murine Leukemia Virus Protease Is Encoded by the Gag-Pol Gene and Is Synthesized through Suppression of an Amber Termination Codon, 82 Proc. Nat'l Acad. Sci. USA 1618–1622 (1985)). Second, +1 frameshifting regulates expression of ornithine decarboxylase antizyme. The system is autoregulatory and depends on the concentration of polyamines (S. Hayashi et al., Ornithine Decarboxylase Antizyme: A Novel Type of Regulatory Protein, 21 Trends Biochem. Sci. 27–30 (1996)). Third, −1 frameshifting is used to synthesize the GagPol precursor polyprotein in retroviruses that have gag, (pro), and pol genes in different reading frames (except spumaretroviruses, J. Enssle et al., Foamy Virus Reverse Transcriptase Is Expressed Independently from the Gag Protein, 93 Proc. Nat'l Acad. Sci. USA 4137–4141 (1996)). Examples are the mouse mammary tumor virus (MMTV) gag-pro frameshift (T. Jacks et al., Two Efficient Ribosomal Frameshifting Events Are Required for Synthesis of Mouse Mammary Tumor Virus Gag-related Polyproteins, 84 Proc. Nat'l Acad. Sci. USA 4298–4302 (1987); R. Moore et al., Complete Nucleotide Sequence of a Milk-transmitted Mouse Mammary Tumor Virus: Two Frameshift Suppression Events Are Required for Translation of Gag and Pol, 61 J. Virol. 480–490 (1987)) and the human immunodeficiency virus type 1 (HIV-1) gag-pol frameshift (N. T. Parkin et al., Human Immunodeficiency Virus Type 1 Gag-Pol Frameshifting Is Dependent on Downstream MRNA Secondary Structure: Demonstration by Expression In Vivo, 66 J. Virol. 5147–5151 (1992)).

Continuous efforts to study the elements on messenger RNAs that signal recoding have led to the development of several reporter systems. In some studies, the efficiency of recoding is assessed by analysis of $^{35}$S-met-labeled translation products. Constructs direct ribosomes to initiate in the zero frame to translate open reading frame-1 (ORF-1). Before the termination of ORF-1, however, a recoding signal in a test sequence directs a proportion of ribosomes to bypass the terminator. In some systems, this occurs by shifting the reading frame; in others, an amino acid is inserted for the stop codon. In both cases, the chimeric product has the upstream reporter fused to the downstream reporter. After electrophoresis of the translation products on an SDS polyacrylamide gel, the ratio of the shorter, upstream product to the chimera reflects the recoding efficiency of the test sequence. Several enzymatic reporter assays have been developed for in vivo studies using chloramphenicol acetyl transferase (cat) (R. Martin et al., Aminoglycoside Suppression at UAG, UAA and UGA Codons in *Escherichia coli* and Human Tissue Culture Cells, 217 Mol. Gen. Genet. 411–418 (1989)) or firefly luciferase (M. Cassan et al., Expression Vectors for Quantitating In Vivo Translational Ambiguity: Their Potential Use to Analyse Frameshifting at the HIV Gag-Pol Junction, 141 Res. Virol. 597–610 (1990); H. Reil & H. Hauser, Test System for Determination of HIV-1 Frameshifting Efficiency in Animal Cells, 1050 Biochim. Biophys. Acta 288–292 (1990)). If the test sequence contains a frameshift signal, its control construct contains a one-base insertion or deletion (in-frame control). If the signal specifies readthrough, in the control, the stop codon is changed into a sense codon by a one-base substitution. Transfection efficiencies are determined by comparison with lacZ gene product from a cotransfected construct.

To obtain a direct measure of efficiency, in two cases (H. Reil et al., A Heptanucleotide Sequence Mediates Ribosomal Frameshifting in Mammalian Cells, 67 J. Virol. 5579–5584 (1993); G. Stahl et al., Versatile Vectors to Study Recoding: Conservation of Rules between Yeast and Mammalian Cells, 23 Nucleic Acids Res. 1557–1560 (1995)) a β-galactosidase reporter gene was inserted in the upstream ORF frame with firefly luciferase downstream providing an internal control for initiating ribosomes. This removed the issue of monitoring transfection efficiencies. The advantage of an activity-based reporter system is that it allows estimation of the ratio between upstream and downstream reporters for the control construct, whereas protein gels only show one product, corresponding to the fusion product. The activity ratio of the positive control can be used to normalize values obtained from the corresponding recoding signal construct. The power of this system, when applied systematically to each construct, is demonstrated in a recent report that showed that the efficiency of HIV-1 frameshifting is directly related to the stability of the stem loop (L. Bidou et al., In Vivo HIV-1 Frameshifting Efficiency Is Directly Related to the Stability of the Stem-Loop Stimulatory Signal, 3 RNA 1153–1158 (1997)). Although β-galactosidase reporters are useful in vivo, they are not suitable for in vitro translation due to the length of the lacZ coding sequence (3 kb).

In view of the foregoing, it will be appreciated that providing a reporter system for in vivo and in vitro measuring translation coupling efficiency of recoding mechanisms such as frameshifting and readthrough would be a significant advancement in the art.

BRIEF SUMMARY OF THE INVENTION

It is an object of the present invention to provide a translational reporter system configured for being used both in vivo and in vitro.

It is another object of the invention to provide a translational reporter system configured for measuring expression of two different luciferases.

It is also an object of the invention to provide a translation reporter system for quantifying translational recoding, reinitiation, and internal initiation in eukaryotes.

It is still another object of the invention to provide a translational reporter system containing a polylinker for insertion of selected genes to be tested.

It is yet another object of the invention to provide a translational reporter system containing a unique linearization site.

These and other objects can be achieved by providing a translational reporter system comprising a vector bearing a polylinker interposed between a first luciferase gene and a second luciferase gene. Preferably, the first luciferase gene is a sea pansy luciferase gene and the second luciferase gene is a firefly luciferase gene. In one preferred embodiment, the translational reporter system is vector p2luc (SEQ ID NO: 1). In another preferred embodiment, the translational reporter system is vector p2luci (SEQ ID NO:2).

The objects of the invention can also be addressed by providing vectors p2luc (SEQ ID NO:1) and p2luci (SEQ ID NO:2).

A method of assaying translational recoding, reinitiation, and internal initiation in vitro comprises
  (a) providing a translational reporter vector comprising a polylinker interposed between first and second luciferase genes wherein the first and second luciferase genes are in different reading frames;
  (b) inserting a DNA to be tested in said reporter vector at the polylinker to form a test vector such that the first and second luciferase genes remain in different reading frames;
  (c) inserting the DNA to be tested in the reporter vector at the polylinker to form a control vector such that the first and second luciferase genes are in the same reading frame;
  (d) separately transcribing the reporter vector, the test vector, and the control vector in vitro to result in respective RNAs comprising transcription copies of the first luciferase gene, the DNA to be tested, and the second luciferase gene;
  (e) separately translating each of the RNAs in vitro to result in translation products thereof;
  (f) determining luminescences attributable each of the translation products, wherein the translation products of the reporter vector contribute background luminescence, the translation products of the control vector contribute normal luminescence, and the translation products of the test vector contribute test luminescence; and
  (g) subtracting background luminescence from the normal and the test luminescences and normalizing the test luminescence with respect to the normal luminescence.

A method of assaying translational recoding, reinitiation, and internal initiation in vivo comprises
  (a) providing a translational reporter vector comprising a polylinker interposed between first and second luciferase genes wherein the first and second luciferase genes are in different reading frames;
  (b) inserting a DNA to be tested in the reporter vector at the polylinker to form a test vector such that the first and second luciferase genes remain in different reading frames;
  (c) inserting the DNA to be tested in the reporter vector at the polylinker to form a control vector such that the first and second luciferase genes are in the same reading frame;
  (d) separately transfecting aliquots of appropriate cells with the reporter vector, the test vector, and the control vector;
  (e) incubating the transfected cells under conditions wherein the vectors are transcribed and translated in vivo;
  (f) lysing the incubated cells and determining luminescences attributable each of the vectors, wherein the reporter vector contributes background luminescence, the control vector contributes normal luminescence, and the test vector contributes test luminescence; and
  (g) subtracting background luminescence from the normal and the test luminescences and normalizing the test luminescence with respect to the normal luminescence.

DETAILED DESCRIPTION

Before the present reporter system and method of use thereof are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise.

In describing and claiming the present invention, the following terminology will be used in accordance with the definitions set out herein.

As used herein, "vector" means a plasmid, virus, or the like that is used in the introduction of DNA or the generation of recombinants.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of."

As used herein, "consisting of" and grammatical equivalents thereof exclude any element, step, or ingredient not specified in the claim.

As used herein, "consisting essentially of" and grammatical equivalents thereof limit the scope of a claim to the specified materials or steps and those that do not materially affect the basic and novel characteristic or characteristics of the claimed invention.

Figure 1:
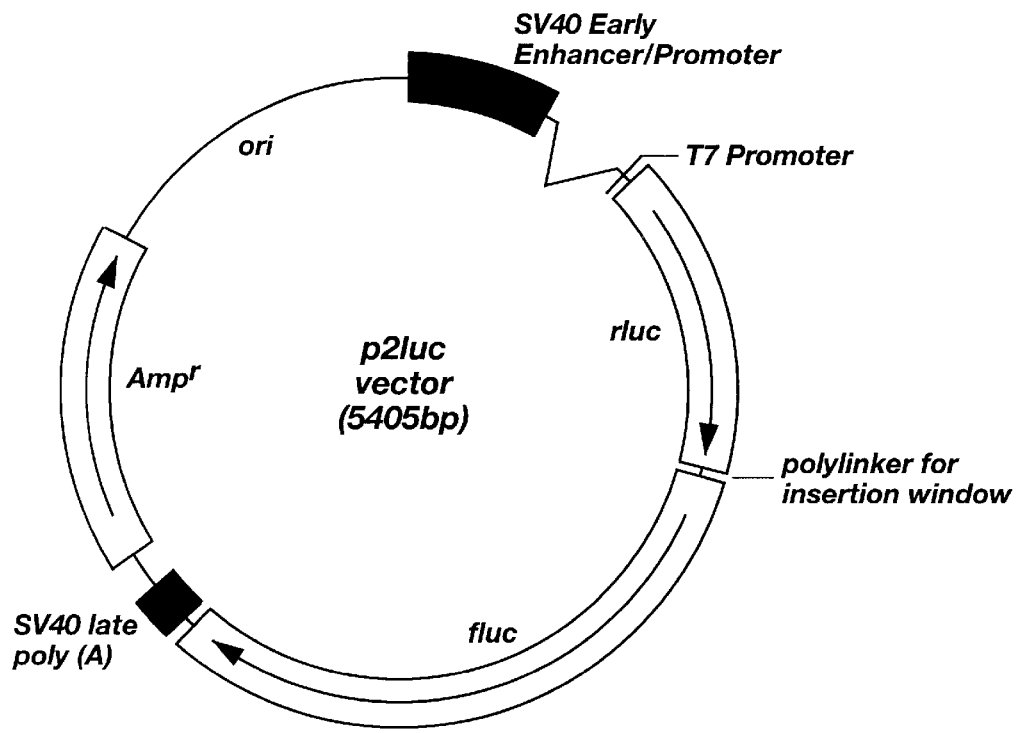
FIGS. 1 and 2 show maps of p2luc and p2luci, respectively, wherein rluc indicates a renilla (sea pansy) luciferase gene; fluc indicates a firefly luciferase gene; $Amp^r$ indicates an ampicillin resistance gene; and ori indicates an origin of replication functional in Escherichia coli, according to the present invention.
Figure 2:
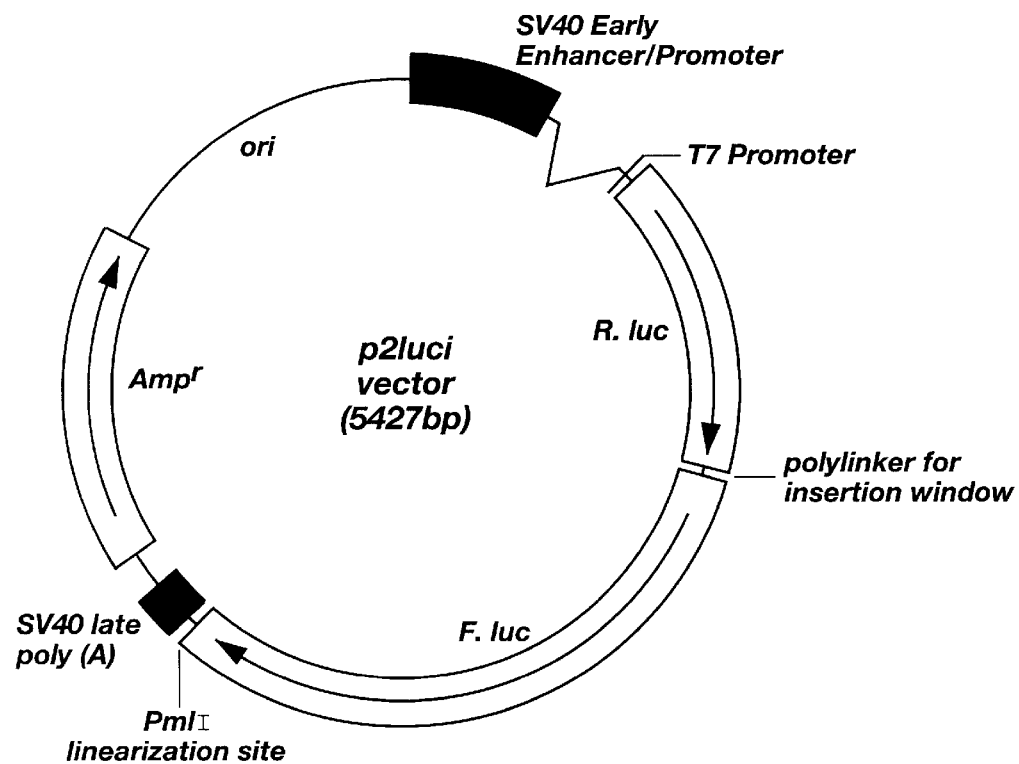

A dual luciferase reporter system for measuring recoding efficiencies in vivo or in vitro from a single construct has been designed (FIGS. 1 and 2). The firefly luciferase gene (fluc) has been cloned behind the renilla luciferase gene (rluc) into an altered vector pRL-SV40 vector (Promega Corp., Madison, Wis; catalog no. TB239; SEQ ID NO:3). Expression features for initiation and termination of transcription and translation, as well as the nature of the two reporter genes (short enough to be efficiently synthesized in an in vitro translation system), allow application of the same reporter construct for in vivo and in vitro applications. Between the 5' reporter (rluc) and the 3' reporter (fluc) two alternative polylinkers have been inserted, yielding p2luc (SEQ ID NO: 1) and p2luci (SEQ ID NO:2). The p2luc polylinker has restriction sites for digestion with SalI, BamHI, and SacI, whereas the p2luci polylinker has restriction sites for digestion with SalI, ApaI, BglII, Eco47III, BamHI, SmaI, and SacI. The assay using these reporter plasmids combines rapidity of the reactions with very low background levels and provides a powerful assay. In vitro experiments can be performed in 96-well microtiter plates, and in vivo experiments can be performed in 6-well culture dishes. This makes the dual-luciferase assay suitable for high throughput screening approaches.

The dual-luciferase assay is designed such that synthesis of the second reporter (firefly luciferase) is dependent on recoding. On its own, however, the amount of this reporter is not a direct reflection of the efficiency of recoding. In the absence of in-frame stop codons, a significant proportion of translating ribosomes disengage prematurely from the mRNA; this is often known as ribosome drop off. Early results from several laboratories have shown that 50% or more of *Escherichia coli* ribosomes drop off during synthesis of β-galactosidase (J. L. Manley, Synthesis and Degradation of Termination and Premature-Termination Fragments of β-Galactosidase In Vitro and In Vivo, 125 J. Mol. Biol. 407–432 (1978); C. G. Kurland et al., Limitations of Translational Accuracy, in F. C. Neidhardt et al., *Escherichia coli* and *Salmonella typhimurium*. Cellular and Molecular Biology 979–1004 ($2^{nd}$ ed. 1996)). Ribosomes that drop off while decoding the firefly reporter will lead to an underestimate of the proportion of ribosomes that respond to the recoding signals unless a correction is made. The basis for a correction factor is the assumption that drop off during synthesis of the firefly reporter is proportional to completion of synthesis of this reporter. The correction factor is provided by a control in which all ribosomes that complete synthesis of the first reporter (renilla luciferase) continue translation by starting synthesis of the firefly luciferase reporter.

The fate of ribosomes is assessed by the level of their products. This can be expressed by the equation $p=RF/(RF+Rf)$, where p is the proportion of ribosomes that respond to the recoding signal that complete synthesis of the firefly reporter; Rf represents the products of translating ribosomes that responded to the recoding signal but aborted before completing synthesis of the firefly reporter; and RF represents products exhibiting firefly luciferase activity (their synthesis requires complete translation of the coding regions for both reporters).

Because the test sequence and its corresponding control are identical downstream of the recoding signal, it is assumed that the proportion, p, is the same for both constructs:

$$=RF_{test}/(RF_{test}+Rf_{test})=RF_{control}/(RF_{control}+Rf_{control}).$$

Recoding efficiency can be expressed by the number of ribosomes that respond to the recoding signal divided by the number of ribosomes that reach the recoding signal (i.e., that have completed translation of the renilla reporter):

$$\text{Recoding efficiency}=(RF_{test}+Rf_{test})/(RF_{test}+Rf_{test}+R_{test})$$

$$=[(RF_{test})/(RF_{test}+Rf_{test}+R_{test})]/p$$

where R is the product of translation of the renilla reporter coding sequence, with ribosomes terminating at the zero frame terminator located at or within a short distance 3' to the site of recoding.

The measured firefly luciferase activity (Fa) is given by the number of peptides that have firefly luciferase activity (RF) multiplied by the specific activity of these peptides (Φ). Because the peptide sequences of a test sequence and its control are identical, the specific activity of molecules synthesized from the test and its control reaction are equal:

$$Fa_{test}=RF_{test}\times\Phi \text{ and } Fa_{control}=RF_{control}\times\Phi.$$

The measured renilla luciferase activity (Ra) is given by the number of peptides that have renilla luciferase activity multiplied by the specific activity (Ω) of the respective species:

$$Ra_{test}=R_{test}\times\Omega_R+Rf_{test}\times\Omega_{Rf}+RF_{test}\times\Omega_{RF} \text{ and}$$

$$Ra_{control}=Rf_{control}\times\Omega_{Rf}+RF_{control}\times\Omega_{RF}.$$

Experimentally, the specific activity of renilla luciferase was not altered by C-terminal extensions of the different constructs (see below). Then:

$$Ra_{test}=(R_{test}+Rf_{test}+RF_{test})\times\Omega \text{ and}$$

$$Ra_{control}=(Rf_{control}+RF_{control})=\Omega.$$

The experimentally established value for the ratio of firefly over renilla luciferase activity for the test sequence can be described as:

$$(Fa_{test}/Ra_{test})=[RF_{test}/(R_{test}+Rf_{test}+RF_{test})]\times[\Phi/\Omega];$$

and the luciferase activity ratio of the control construct as:

$$(Fa_{control}/Ra_{control})=[RF_{control}/(Rf_{control}+RF_{control})]\times[\Phi\Omega]$$

$$=p\times\Phi/\Omega.$$

It follows that:

Recoding efficiency=$[(RF_{test})/(RF_{test}+Rf_{test}+R_{test})]/p$ $=(Fa_{test}/Ra_{test})/(Fa_{control}/Ra_{control})$.

In other words, the activity ratio of the control construct can be used to normalize the activity ratio obtained from the test sequence for drop off occurring downstream from the recoding signal.

Figure 3:
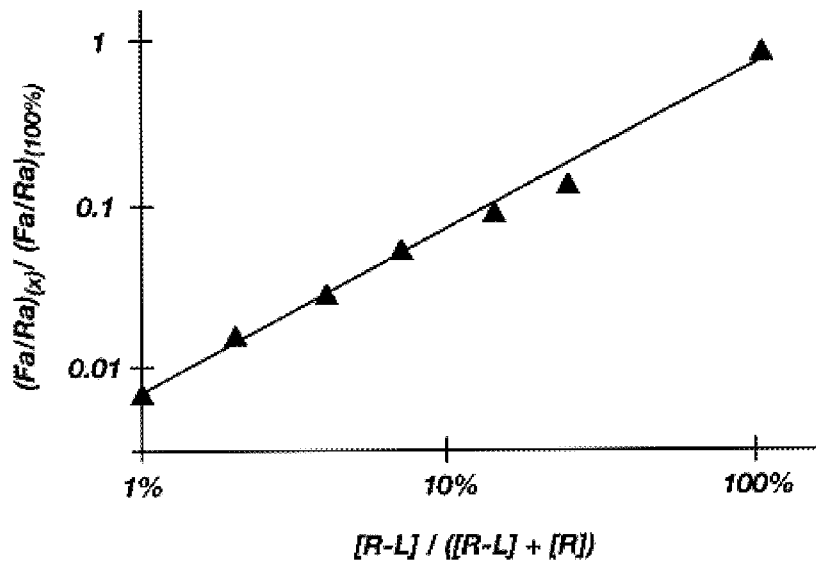
FIG. 3 shows that reporter activities are proportional to in vitro translation of their mRNAs: in vitro reticulocyte lysate reactions were performed as described in Example 3 in the presence of 1 μg of RNA mixtures containing different percentages of HIV-1 in-frame control RNA (R-L) and the out-of-frame control p2luc RNA (R); firefly/renilla activity ratios (Fa/Ra) were normalized to the reaction containing 100% (R-L).

The above calculation of frameshift efficiency is based on the assumption that the specific activity of renilla luciferase is not altered by C-terminal elongation of the protein. Comparison of the radioactivity levels from $^{35}S$-labeled translation products, electrophoresed on SDS polyacrylamide gels, with activity-assay values showed no significant alterations. On the other hand, estimation of the amount of Rf by phosphorimaging is relatively imprecise, due to the large area of the gel containing Rf products. Another way to verify that the specific activity of renilla luciferase is not altered by a C-terminal extension is to establish a dose-response curve comparing reactions with different amounts of out-of-frame and in-frame mRNA. If the renilla activity is not altered by C-terminal extension, the firefly/renilla luciferase activity ratios (Ra/Fa) of the reactions should be linear and proportional to the amount of in-frame mRNA. If, on the contrary, C-terminal extension diminishes the specific activity of renilla luciferase, a nonlinear (concave) increase of the ratio would be expected. FIG. 3 shows that reporter activities are proportional to in vitro translation of their mRNAs (Example 3).

Vectors p2luc and p2luci were designed to allow recoding assays in vitro and in vivo. The plasmids contain major expression features of pRSV40: an SV40 early enhancer/promoter initiates transcription in eukaryotic cells. A chimeric intron increases transport of the messenger into the cytoplasm. The second reporter gene is followed by an SV40 late polyadenylation signal. Insertion of a T7 promoter in front of the renilla luciferase gene (rluc) and a blunt end restriction site behind firefly luciferase (fluc) provide the means to permit in vitro transcription.

EXAMPLE 1

General procedures for DNA recombination techniques, plasmid extractions, and the like were performed as described in J. Sambrook et al., Molecular Cloning: A Laboratory Manual (2d ed., 1989), the relevant portions of which are hereby incorporated by reference. All vectors were transformed into E. coli strain SU1675. The unique BglII site in pRL-SV40 (Promega Corp., Madison, Wis.; cat. no. TB239; SEQ ID NO:3) was cut and filled in by T4 DNA polymerase. The resulting blunt ends were religated, giving pG11.

PCR primers lucR (SEQ ID NO:4) and Xcm (SEQ ID NO:5) were synthesized on an Applied Biosystems model 380C automated synthesizer. PCR was then carried according to methods well known in the art, e.g., U.S. Pat. No. 4,683,195; U.S. Pat. No. 4,683,202; U.S. Pat. No. 4,800,159; U.S. Pat. No. 4,965,188; PCR Technology: Principles and Applications for DNA Amplification (H. Erlich ed., Stockton Press, New York, 1989); PCR Protocols: A guide to Methods and Applications (Innis et al. eds, Academic Press, San Diego, Calif., 1990), using primers lucR and Xcm with pRL-SV40 as template. The PCR product was digested with BglII and XcmI and then inserted between the unique BamHI and XcmI sites of pG11, thereby replacing the unique BamHI site and inserting unique PmeI and SalI sites. The resulting plasmid was designated pG12. The firefly luciferase gene from pBgalluc-1 (obtained from Dr. H. Hauser), H. Reil, 67 J. Virol. 5579–84 (1993), hereby incorporated by reference, was recloned in plasmid pNewcite between BamHI and PmeI sites. A BamHI-PmeI restriction fragment containing the firefly luciferase gene was then inserted between the BamHI and PmeI sites of pG12, resulting in plasmid pG13. A blunt-end linearization site behind the firefly luciferase reading frame was added, and the transcriptional terminator was reinstalled by cloning the PCR product resulting from amplification of pRL-SV40 with primers 2lucA1 (SEQ ID NO:6) and 2lucA2 (SEQ ID NO:7) between the EcoNI and PmeI sites of pG13, resulting in the plasmid p2luc (FIG. 1; SEQ ID NO: 1; Gene Bank accession no. AF043450).

EXAMPLE 2

A second version (p2luci) of the reporter plasmid of the present invention, with supplemental cloning sites, was constructed by inserting the annealing product of complementary primers luci1 (SEQ ID NO:8) and luci2 (SEQ ID NO:9) between the SalI and NarI sites of p2luc. The sequence of p2luci is designated herein as SEQ ID NO:2.

EAXMPLE 3

Translation assays were performed in reticulocyte lysates with increasing amounts of an HIV in-frame control RNA (R-L) compared to the 2luc out-of-frame RNA (R). The HIV (strain HXB-2) in-frame control was generated by amplifying pGEM3ZPS (obtained from Dr. X. F. Yu) using the primers SAA2luc (SEQ ID NO: 10), which generates a SalI site, and BglP1 (SEQ ID NO: 11), which generates a BglII site. The PCR product was cloned between the unique SalI and BamHI sites of p2luc. The sequence of the construct was verified by automated thermocycler sequencing.

For in vitro transcription, PmlI-linearized plasmids were used as templates for T7 RNA polymerase according to methods well known in the art, e.g., N. M. Wills et al., Evidence that a Downstream Pseudoknot Is Required for Translational Read-Through of the Moloney Murine Leukemia Virus Gag Stop Codon, 88 Proc. Nat'l Acad. Sci. USA 6991–6995 (1991) (hereby incorporated by reference). For in vitro translation in reticulocyte lysate (Promega Corp.), 1 $\mu$g of each RNA preparation was used per 7.5 $\mu$l of reaction mixture, complemented at 130 $\mu$M with all amino acids except methionine, and 3.3 $\mu$M ($^{35}S$)-met (1,200 mCi/mM) was added. For luciferase activity measurements, samples of 3 $\mu$l or 0.6 $\mu$l of reticulocyte lysate mixtures were diluted in 100 $\mu$l of 1 X lysis buffer and analyzed for renilla and firefly luminescence activity using the Dual-Luciferase™ reporter assay (Promega Corp.) on a Dynatech MLX Microtiter Plate Luminometer. For both reactions, light emission was measured between 2 and 12 seconds after luminescence substrate injection. In a first reaction, extracts were tested for firefly luciferase activity in the presence of beetle luciferin, $O^2$, and $Mg^{2+}$, via a luciferyl-coA intermediate, which allows rapid enzymatic turnover. In a second step, firefly luciferase activity was quenched and the substrate of renilla luciferase (Coelenterazine) was added. To avoid contamination between the firefly reagent and its quenching reagent (in the second step), all 96 wells of one microtiter plate were tested for luciferase activity before starting measurement of renilla luciferase.

As controls, luciferase activity reactions were performed with and without 130 $\mu$M of supplemented methionine (the endogenous concentration of methionine in reticulocyte lysate is 5 μM). No differences in overall translational efficiency or recoding efficiency were observed.

In vitro assays were performed four times with two independent RNA preparations.

Renilla and firefly luciferase activities were assayed in the same tube. Standard deviations of established activity ratios, therefore, were independent of volume variations due to pipetting. Standard deviation for recoding efficiencies established in vitro was less than 20% of the values.

FIG. 3 shows the results of in vitro reticulocyte lysate reactions performed as described above in the presence of 1 μg of RNA mixtures containing different percentages of HIV-1 in-frame control RNA (R-L) and the out-of-frame control p2luc-RNA (R). Firefly/renilla activity ratios (Fa/Ra) were normalized to the reaction containing 100% (R-L) RNA. The firefly/renilla luciferase activity ratios were linear over two orders of magnitude and were proportional to the reaction containing 100% (R-L) mRNA.

EXAMPLE 4

In this example, the dual-luciferase assay was applied to four different recoding systems: (a) −1 frameshifting (HIV gag-pol), (b) −1 frameshifting (MMTV gag-pro), (c) readthrough (MULV gag-pol), and (d)+1 frameshifting (antizyme).

For constructs containing the recoding sequences of MuLV and MMTV, complementary oligonucleotides with SalI and BamHI compatible ends were synthesized on an Applied Biosystems model 380C synthesizer. These oligonucleotides were as follows: MMTV (SEQ ID NO:12); MMTV control (SEQ ID NO:13); MULV (SEQ ID NO: 14); MULV control (SEQ ID NO: 15). For HIV-1 (strain HSB-2), PCR primers SAA2luc (SEQ ID NO: 10) and B1Gpr (SEQ ID NO:16), containing SalI and BamHI restriction sites, were used to amplify the wild-type sequence from pGEM3ZPS. For cloning the antizyme test sequence, oligonucleotides fsAZ1 (SEQ ID NO: 17) and sfAZ2 (SEQ ID NO: 18), containing SalI and BamHI sites, to generate wild-type and in-frame control sequences from AY103 and AYFC01 (obtained from Dr. S. Matsufuji), respectively, by PCR. S. Matsufuji et al., Reading Two Bases Twice: Mammalian Antizyme Frameshifting in Yeast, 15 EMBO J. 1360–1370 (1996) (hereby incorporated by reference). For HIV-1 (strain HXB-2), the wild-type sequence was generated by amplifying pGEM3ZPS (obtained from Dr. X. F. Yu) using the primers SAA2luc (SEQ ID NO: 10), which generates a SalI site, and B lGpr (SEQ ID NO: 16), which generates a BglII site. An HIV-1 in-frame control was generated according to the procedure of Example 3. PCR products were cloned between the unique SalI and BamHI sites of p2luc. The sequences of all constructs were verified by automated thermocycler sequencing.

For in vitro translations, the procedure of Example 3 was used except that, after translation, samples were also electrophoresed on SDS/15% polyacrylamide gels in addition to determining luminescences. Dried gels were scanned and quantified for radioactivity on a Molecular Dynamics PhosphorImager.

For in vivo translations, human kidney 293 cells (ATCC) were cultivated in minimum essential medium supplemented with 10% fetal bovine serum. Transient transfections were performed by lipofection using reagents from GIBCO/BRL (Gaithersburg, Md.). In vivo expression of the reporter genes was dependent on cell density and transfection efficiency, but was consistent in a given series of transfection experiments. Luciferase activity was determined 24 hours after transfection. One-hundred microliters of lysate was assayed by the Dual-Luciferase™ reporter assay as described above. In vivo recoding experiments were repeated four or six times in two or three different transfection series.

The p2luc vector without any insertion has the firefly luciferase gene in the −1 frame, and ribosomes translating the upstream renilla luciferase gene are stopped at the sixth codon behind the SalI cloning site. The HIV test construct contained a 307 nucleotide insertion covering the entire overlapping sequence between gag and pol. Ribosomes that do not shift to the −1 frame stop at codon 95 of the test sequence. The in-frame construct has a one-base insertion leading translating ribosomes into the −1 frame, and two single-base substitutions that destroy the slippery sequence and prevent frameshifting into the −2 frame. The MMTV test sequence works very similarly. Ribosomes that do not shift are stopped at the fourth codon behind the recoding signal, but ribosomes that have shifted to the −1 frame translate into the firefly luciferase coding sequence. Again, the control construct has a one-base insertion and destroyed the slippery sequence. The MuLV recoding signal features an in-frame stop codon. Ribosomes that read through this stop codon continue translation and enter the firefly luciferase reporter. The control sequence has a stop codon, UAG, replaced with CAG, which codes for glutamine. The antizyme recoding signal contains an in-frame stop codon, which ribosomes can avoid by a +1 frameshift. The control has an insertion of two bases, putting the stop codon out-of-frame and leading translating ribosomes into the +frame.

Figure 4:
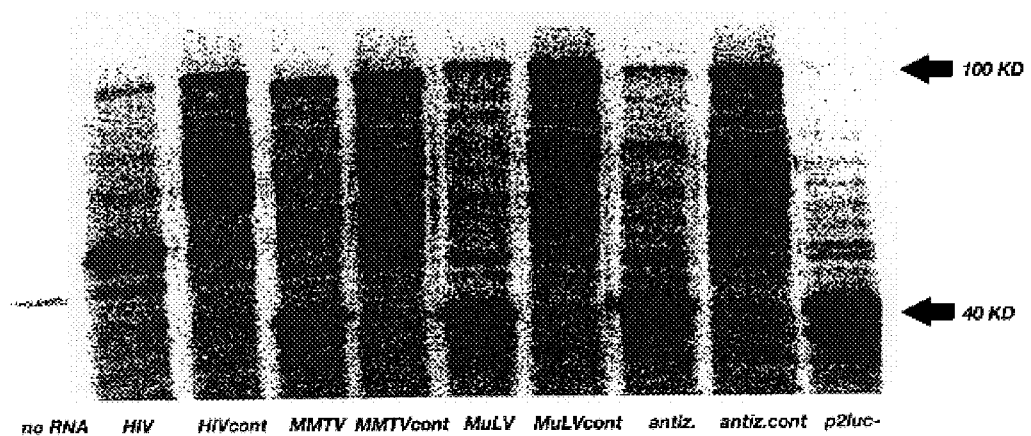
FIG. 4 shows an autoradiograph of four recoding systems by the dual-luciferase reporter.

FIG. 4 shows the results of SDS polyacrylamide electrophoresis of products of an in vitro translation. These results can be compared to recoding efficiencies in vitro (Table 1) and in vivo (Table 2) that were calculated from luciferase activity measurements. In vitro, renilla luciferase corresponded to a 40-kDa translation product on a protein gel, and firefly luciferase activity was proportional to a product of 100 kDa. Thus, activity of the firefly luciferase reporter was due to the expression of a fusion protein, which depended on the recoding efficiency of the different test sequences.

TABLE 1

| In vitro | Fa/Ra | Rec.-eff. (%) | Prev. Rep. (%) |
|---|---|---|---|
| HIV | 0.021 | 7.1 | 11[a,b] |
| HIV$_{cont}$ | 0.258 | | |
| MMTV | 0.299 | 29 | 15–25[c], 23[d] |
| MMTV$_{cont}$ | 1.026 | | |
| MuLV | 0.069 | 8.8 | 5[e] |
| MuLV$_{cont}$ | 0.75 | | |
| Antizyme | 0.025 | 3.6 | 3, (18–30)*[f] |
| Antizyme$_{cont}$ | 0.614 | | |
| p2luc | 0.003 | — | — |

[a]T. Jacks et al., Characterization of Ribosomal Frameshifting in HIV-1 Gag-Pol Expression, 331 Nature 280–283 (1988).
[b]H. Reil et al., supra.
[c]R. Moore et al., supra.
[d]T. Jacks et al., et al., 84 Proc. Nat'l Acad. Sci. USA 4298–4302 (1987), supra.
[e]N. M. Wills et al., supra.
[f]S. Matsufuji et al., Autoregulatory Frameshifting in Decoding Ornithine Decarboxylase Antizyme, 80 Cell 51–60 (1995) (*when supplemented with 0.8 mM spermidine).

TABLE 2

| In vivo | Fa/Ra | Rec.-eff. (%) | Prev. rep. (%) |
|---|---|---|---|
| HIV | 0.022 | 2.8 | 2–4[a], 1–2[b] |
| HIV$_{cont}$ | 0.752 | | |
| MMTV | 0.433 | 18 | — |
| MMTV$_{cont}$ | 2.357 | | |
| MuLV | 0.082 | 3.7 | 5[c] |
| MuLV$_{cont}$ | 2.174 | | |
| Antizyme | 0.825 | 40 | ~35[d] |
| Antizyme$_{cont}$ | 2.076 | | |
| p2luc | 0.001 | — | — |

[a]H Reil et al., supra.
[b]M. Casan et al., supra.
[c]Y. X. Feng et al., Identification of Amino Acids Inserted during Suppression of UAA and UGA Termination Codons at the Gag-Pol Junction of Moloney Murine Leukemia Virus, 87 Proc. Nat'l Acad. Sci. USA 8860–8863 (1990).
[d]S. Matsufuji.

Recoding efficiencies (Rec.-eff.) determined by the dual-luciferase reporter were very comparable to previously reported values (prev. rep.). In vitro, HIV gag-pol frameshifting (7.1%) was a little lower than what was reported (11%). MMTV gag-pol (29%) and MuLV gag-pol (8.8%) recoding values were somewhat higher than previous data (15–25% and 5%, respectively). Antizyme frameshifting (3.6%) at the endogenous polyamine concentration of reticulocyte lysate corresponded well to what was reported (~3%).

In vivo, results obtained with the 2-luciferase reporter for HIV (2.8%) and antizyme (40%) were close to data reported by others (1–4% and 35%, respectively). MuLV readthrough (3.7%) was slightly lower than reported previously (5%). For MMTV frameshifting in vivo, 18% was obtained. It is believed that no quantitative estimation for MMTV in vivo frameshifting has previously been reported.

The frameshift efficiency for antizyme was 10 times lower, in vitro (3.6%) than in vivo (40%). In vivo frameshifting can be amplified up to 10 times by supplementing reticulocyte lysate with polyamines (S. Matsufuji et al., 80 Cell 51–60 (1995), supra). In vivo, antizyme frameshifting is high, presumably due to high intracellular concentration of polyamines. By controlling the intracellular polyamine concentration, similar dependence of antizyme frameshifting on polyamine concentrations has been observed in transfected mammalian cells.

For the three retroviral systems (HIV, MMTV, and MuLV), recoding efficiencies were observed to be lower in vivo than in vitro. The three systems contain a stimulatory secondary structure 3' to the recoding site, which might partially act by inducing ribosomal pausing (C. Tu et al., Ribosomal Movement Impeded at a Pseudoknot Required for Frameshifting, 89 Proc. Nat'l Acad. Sci. USA 8636–8640 (1992); P. Somogyi et al., Ribosomal Pausing during Translation of an RNA Pseudoknot, 13 Mo. Cell. Biol. 6931–6940 (1993)). One possible explanation is that, under suboptimal in vitro conditions, the effect of ribosomal stalling has a higher impact than in vivo.

Luciferase activity ratios for the control constructs varied with the test sequence. Overall processivity of the dual-luciferase reporter system was significantly higher in vivo than in vitro. Nevertheless, variations of translation efficiencies, which were observed in vitro, were conserved in vivo (compare Fa/Ra values of control constructs in Table 1 and Table 2). Specifically, the HIV frameshift window significantly lowered translation processivity, which may be due to the length of the inserted sequence.

A general concern when using any reporter system is that artifactual results may arise occasionally from interactions between test and reporter sequences. Such artifacts can be controlled by comparing with the results from a different reporter system. The fact that previous and present results correspond gives confidence in the obtained results.

The dual-luciferase assay of the present invention gave an in vitro background value for nonspecific recoding of about 0.3% for the out-of-frame control (p2luc, Table 1). The background in vivo (p2luc, Table 2) was much lower (0.1%).

In summary, the dual-luciferase assay of the present invention allows the obtaining of reliable numbers that are likely to quite accurately measure the efficiency of recoding for a given test sequence, both in vivo and in vitro. This is achieved by normalizing reporter activity ratios of recoding windows by their corresponding in-frame control. Linear activity ratios from 100% to less than 1% have been shown. The low background of the luciferase reactions allows quantitation of coupling of two translational cistrons in vivo and in vitro at efficiencies down to 0.1%. The rapidity and the accuracy of the assay make it a suitable tool for research on recoding signals, but also for applications in drug screening where translation recoding is targeted.

We claim:

1. A translational reporter vector comprising a polylinker interposed between a renilla luciferase gene and a firefly luciferase gene, wherein the renilla luciferase gene and the firefly luciferase gene are out-of-frame with respect to each other but are co-expressed upon recoding, wherein said translational reporter vector is a member selected from the group consisting of p2luc (SEQ ID NO:1) and p2luci (SEQ ID NO:2).

2. The vector p2luc (SEQ ID NO:1).

3. The vector p2luci (SEQ ID NO:2).

4. A method of assaying translational recoding in vitro comprising
   (a) providing a translational reporter vector comprising a polylinker interposed between first and second luciferase genes wherein said first and second luciferase genes are in different reading frames;
   (b) inserting a DNA to be tested in said reporter vector at the polylinker to form a test vector such that the first and second luciferase genes remain in different reading frames;
   (c) inserting the DNA to be tested in said reporter vector at the polylinker to form a control vector such that the first and second luciferase genes are in the same reading frame;
   (d) separately transcribing said reporter vector, said test vector, and said control vector in vitro to result in respective RNAs comprising transcription copies of said first luciferase gene, said DNA to be tested, and said second luciferase gene;
   (e) separately translating each of said RNAs in vitro to result in translation products thereof;
   (f) determining luminescences attributable to each of said translation products, wherein the translation products of the reporter vector contribute background luminescence, the translation products of the control vector contribute normal luminescence, and the translation products of the test vector contribute test luminescence; and
   (g) subtracting background luminescence from said normal and said test luminescences and normalizing said test luminescence with respect to said normal luminescence.

5. The method of claim 4 wherein said translational reporter vector is p2luc (SEQ ID NO:1).

6. The method of claim 4 wherein said translational reporter vector is p2luci (SEQ ID NO:2).

7. A method for assaying translational recoding in vivo comprising:
   (a) providing a translational reporter vector comprising a polylinker interposed between first and second luciferase genes wherein said first and second luciferase genes are in different reading frames and wherein said translational reporter vector is a member selected from the group consisting of p2luc (SEQ ID NO:1) and p2luci (SEQ ID NO:2);
   (b) inserting a DNA to be tested in said translational reporter vector at the polylinker to form a test vector such that the first and second luciferase genes remain in different reading frames;
   (c) inserting the DNA to be tested in said translational reporter vector at the polylinker to form a control vector such that the first and second luciferase genes are in the same reading frame;
   (d) separately transfecting aliquots of cells with said translational reporter vector, said test vector, and said control vector;
   (e) incubating the transfected cells under conditions wherein the vectors are transcribed and translated in vivo;
   (f) lysing said incubated cells and determining luminescences attributable to each of said vectors, wherein the translational reporter vector contributes background luminescence, the control vector contributes normal luminescence, and the test vector contributes test luminescence; and
   (g) subtracting background luminescence from said normal and said test luminescences and normalizing the background-subtracted test luminescence with respect to the background-subtracted normal luminescence.

8. The method of claim 7 wherein said translational reporter vector is p2luc (SEQ ID NO: 1).

9. The method of claim 7 wherein said translational reporter vector is p2luci (SEQ ID NO:2).

10. A translational reporter vector configured for assaying translational recoding in vitro and in vivo, comprising a polylinker interposed between a first luciferase coding sequence and a second luciferase coding sequence, a eukaryotic promoter and a non-eukaryotic promoter each disposed upstream of said first luciferase coding sequence, a polyadenylation signal and transcriptional terminator disposed downstream of said second luciferase coding sequence, and a linearization site disposed downstream of said second luciferase coding sequence, wherein the first luciferase coding sequence and the second luciferase coding sequence are out-of-frame with respect to each other but are co-expressed upon recoding.

11. The translational reporter vector of claim 10 wherein said first luciferase coding sequence encodes a renilla luciferase.

12. The translational reporter vector of claim 10 wherein said second luciferase coding sequence encodes a firefly luciferase.

13. The translational reporter vector of claim 10 wherein said eukaryotic promoter comprises an SV40 early promoter and enhancer.

14. The translational reporter vector of claim 10 wherein said non-eukaryotic promoter comprises a T7 promoter.

15. A method for assaying translational recoding in vitro comprising:
   (a) providing a translational reporter vector configured for assaying translational recoding in vitro and in vivo, comprising a polylinker interposed between a first luciferase coding sequence and a second luciferase coding sequence, a eukaryotic promoter and a non-eukaryotic promoter each disposed upstream of said first luciferase coding sequence, a polyadenylation signal and transcriptional terminator disposed downstream of said second luciferase coding sequence, and a linearization site disposed downstream of said second luciferase coding sequence, wherein the first luciferase coding sequence and the second luciferase coding sequence are out-of-frame with respect to each other but are co-expressed upon recoding;

(b) inserting a DNA to be tested in said translational reporter vector at the polylinker to form a test vector such that the first and second luciferase coding sequences remain in different reading frames;

(c) inserting the DNA to be tested in said translational reporter vector at the polylinker to form a control vector such that the first and second luciferase coding sequences are in the same reading frame;

(d) separately linearizing at the linearization site and then transcribing said translational reporter vector, said test vector, and said control vector in vitro to result in respective RNAs comprising transcription copies of said first luciferase coding sequence, said DNA to be tested, and said second luciferase coding sequence;

(e) separately translating each of said RNAs in vitro to result in translation products thereof comprising said first and second luciferases; and (f) determining amounts of luminescence attributable to each of said first and second luciferases, subtracting background from said amounts of luminescence, and then calculating an activity ratio of the second luciferase to the first luciferase, each produced from the test vector, normalized by an activity ratio of the second luciferase to the first luciferase, each produced from the control vector.

16. The method of claim 15 wherein said first luciferase coding sequence encodes a renilla luciferase.

17. The method of claim 15 wherein said second luciferase coding sequence encodes a firefly luciferase.

18. The method of claim 15 wherein said non-eukaryotic promoter comprises a T7 promoter.

19. The method of claim 15 wherein said translational reporter vector is p2luc (SEQ ID NO:1).

20. The method of claim 15 wherein said translational reporter vector is p2luci (SEQ ID NO:2).

21. A method for assaying translational recoding in vivo comprising:

(a) providing a translational reporter vector configured for assaying translational recoding in vitro and in vivo, comprising a polylinker interposed between a first luciferase coding sequence and a second luciferase coding sequence, a eukaryotic promoter and a non-eukaryotic promoter each disposed upstream of said first luciferase coding sequence, a polyadenylation signal and transcriptional terminator disposed downstream of said second luciferase coding sequence, and a linearization site disposed downstream of said second luciferase coding sequence, wherein the first luciferase coding sequence and the second luciferase coding sequence are out-of-frame with respect to each other but are co-expressed upon recoding;

(b) inserting a DNA to be tested in said translational reporter vector at the polylinker to form a test vector such that the first and second luciferase coding sequences remain in different reading frames;

(c) inserting the DNA to be tested in said translational reporter vector at the polylinker to form a control vector such that the first and second luciferase coding sequences are in the same reading frame;

(d) separately transfecting aliquots of cells with said translational reporter vector, said test vector, and said control vector;

(e) incubating the transfected cells under conditions wherein the vectors are transcribed and translated in vivo; and (f) lysing said incubated cells and determining amounts of luminescence attributable to each of said first and second luciferases, subtracting background from said amounts of luminescence, and then calculating an activity ratio of the second luciferase to the first luciferase, each produced from the test vector, normalized by an activity ratio of the second luciferase to the first luciferase, each produced from the control vector.

22. The method of claim 21 wherein said first luciferase coding sequence encodes a renilla luciferase.

23. The method of claim 21 wherein said second luciferase coding sequence encodes a firefly luciferase.

24. The method of claim 21 wherein said eukaryotic promoter comprises an SV40 early promoter and enhancer.

25. The method of claim 21 wherein said translational reporter vector is p2luc (SEQ ID NO:1).

26. The method of claim 21 wherein said translational reporter vector is p2luci (SEQ ID NO:2).

* * * * *

UNITED STATES PATENT AND TRADEMARK OFFICE
CERTIFICATE OF CORRECTION

PATENT NO. : 6,143,502
DATED : November 7, 2000
INVENTOR(S) : Guido Grentzmann; Raymond F. Gesteland; John F. Atkins It is certified that error appears in the above-identified patent and that said Letters Patent is hereby corrected as shown below:

On the front page, after the name of inventor John F. Atkins, "Verrières le Buisson, France" should read --Salt Lake City, Utah--.

At column 2, line 8, "MRNA" should read --mRNA--.

At column 3, line 61, insert --to-- prior to "each".

At column 6, line 21, --p-- should appear to the left of "=".

At column 6, line 57, the portion of the formula reading "=$\Omega$" should read --x $\Omega$--.

At column 6, line 65, the portion of the formula reading "$\Phi\Omega$" should read --$\Phi/\Omega$--.

At column 8, line 25, "EAXMPLE" should read --EXAMPLE--.

At column 9, line 39, insert --were used-- prior to "to generate".

At column 9, line 48, "B 1Gpr" should read --B1Gpr--.

Signed and Sealed this

First Day of May, 2001

Attest:

NICHOLAS P. GODICI

Attesting Officer

Acting Director of the United States Patent and Trademark Office

SEQUENCE LISTING

```
<160> NUMBER OF SEQ ID NOS: 18

<210> SEQ ID NO 1
<211> LENGTH: 5405
<212> TYPE: DNA
<213> ORGANISM: Artificial Sequence
<220> FEATURE:
<223> OTHER INFORMATION: p2luc

<400> SEQUENCE: 1
agatcgatct gcgcagcacc atggcctgaa ataacctctg aaagaggaac          50
ttggttaggt accttctgag gcggaagaa ccagctgtgg aatgtgtgtc           100
agttagggtg tggaaagtcc ccaggctccc cagcaggcag aagtatgcaa          150
agcatgcatc tcaattagtc agcaaccagg tgtggaaagt ccccaggctc          200
```

-continued

| | |
|---|---|
| cccagcaggc agaagtatgc aaagcatgca tctcaattag tcagcaacca | 250 |
| tagtcccgcc cctaactccg cccatcccgc ccctaactcc gcccagttcc | 300 |
| gcccattctc cgccccatgg ctgactaatt tttttatttt atgcagaggc | 350 |
| cgaggccgcc tcggcctctg agctattcca gaagtagtga ggaggctttt | 400 |
| ttggaggcct aggcttttgc aaaaagcttg attcttctga cacaacagtc | 450 |
| tcgaacttaa gctgcagaag ttggtcgtga ggcactgggc aggtaagtat | 500 |
| caaggttaca agacaggttt aaggagacca atagaaactg ggcttgtcga | 550 |
| gacagagaag actcttgcgt ttctgatagg cacctattgg tcttactgac | 600 |
| atccactttg cctttctctc acaggtgtc cactcccagt tcaattacag | 650 |
| ctcttaaggc tagagtactt aatacgactc actataggct agccaccatg | 700 |
| acttcgaaag tttatgatcc agaacaaagg aaacggatga taactggtcc | 750 |
| gcagtggtgg gccagatgta aacaaatgaa tgttcttgat tcatttatta | 800 |
| attattatga ttcagaaaaa catgcagaaa atgctgttat tttttttacat | 850 |
| ggtaacgcgg cctcttctta tttatggcga catgttgtgc cacatattga | 900 |
| gccagtagcg cggtgtatta taccagacct tattggtatg ggcaaatcag | 950 |
| gcaaatctgg taatggttct tataggttac ttgatcatta caaatatctt | 1000 |
| actgcatggt ttgaacttct taatttacca aagaagatca tttttgtcgg | 1050 |
| ccatgattgg ggtgcttgtt tggcatttca ttatagctat gagcatcaag | 1100 |
| ataagatcaa agcaatagtt cacgctgaaa gtgtagtaga tgtgattgaa | 1150 |
| tcatgggatg aatggcctga tattgaagaa gatattgcgt tgatcaaatc | 1200 |
| tgaagaagga gaaaaaatgg ttttggagaa taacttcttc gtggaaacca | 1250 |
| tgttgccatc aaaaatcatg agaaagttag aaccagaaga atttgcagca | 1300 |
| tatcttgaac cattcaaaga gaaggtgaa gttcgtcgtc caacattatc | 1350 |
| atggcctcgt gaaatcccgt tagtaaaagg tggtaaacct gacgttgtac | 1400 |
| aaattgttag gaattataat gcttatctac gtgcaagtga tgatttacca | 1450 |
| aaaatgttta ttgaatcgga cccaggattc ttttccaatg ctattgttga | 1500 |
| aggtgccaag aagttttccta atactgaatt tgtcaaagta aaaggtcttc | 1550 |
| attttttcgca agaagatgca cctgatgaaa tgggaaaata tatcaaatcg | 1600 |
| ttcgttgagc gagttctcaa aaatgaacaa atgtcgacgg atccttcaac | 1650 |
| ttccctgagc tcgaagacgc caaaaacata agaaaggcc cggcgccatt | 1700 |
| ctatcctcta gaggatggaa ccgctggaga gcaactgcat aaggctatga | 1750 |
| agagatacgc cctggttcct ggaacaattg cttttacaga tgcacatatc | 1800 |
| gaggtgaaca tcacgtacgc ggaatacttc gaaatgtccg ttcggttggc | 1850 |
| agaagctatg aaacgatatg ggctgaatac aaatcacaga atcgtcgtat | 1900 |
| gcagtgaaaa ctctcttcaa ttctttatgc cggtgttggg cgcgttattt | 1950 |
| atcggagttg cagttgcgcc cgcgaacgac atttataatg aacgtgaatt | 2000 |
| gctcaacagt atgaacattt cgcagcctac cgtagtgttt gtttccaaaa | 2050 |
| agggggttgca aaaatttttg aacgtgcaaa aaaaattacc aataatccag | 2100 |
| aaaattatta tcatggattc taaaacggat taccagggat ttcagtcgat | 2150 |
| gtacacgttc gtcacatctc atctacctcc cggttttaat gaatacgatt | 2200 |

-continued

```
ttgtaccaga gtcctttgat cgtgacaaaa caattgcact gataatgaat       2250
tcctctggat ctactgggtt acctaagggt gtggcccttc cgcatagaac       2300
tgcctgcgtc agattctcgc atgccagaga tcctattttt ggcaatcaaa       2350
tcattccgga tactgcgatt ttaagtgttg ttccattcca tcacggtttt       2400
ggaatgttta ctacactcgg atatttgata tgtggatttc gagtcgtctt       2450
aatgtataga tttgaagaag agctgttttt acgatccctt caggattaca       2500
aaattcaaag tgcgttgcta gtaccaaccc tattttcatt cttcgccaaa       2550
agcactctga ttgacaaata cgatttatct aatttacacg aaattgcttc       2600
tgggggcgca cctctttcga aagaagtcgg ggaagcggtt gcaaaacgct       2650
tccatcttcc agggatacga caaggatatg ggctcactga gactacatca       2700
gctattctga ttacacccga gggggatgat aaaccgggcg cggtcggtaa       2750
agttgttcca ttttttgaag cgaaggttgt ggatctggat accgggaaaa       2800
cgctgggcgt taatcagaga ggcgaattat gtgtcagagg acctatgatt       2850
atgtccggtt atgtaaacaa tccggaagcg accaacgcct tgattgacaa       2900
ggatggatgg ctacattctg gagacatagc ttactgggac gaagacgaac       2950
acttcttcat agttgaccgc ttgaagtctt taattaaata caaggatat        3000 caggtggccc ccgctgaatt ggaatcgata ttgttacaac accccaacat       3050
cttcgacgcg ggcgtggcag gtcttcccga cgatgacgcc ggtgaacttc       3100
ccgccgccgt tgttgttttg gagcacgaaa agacgatgac ggaaaaagag       3150
atcgtggatt acgtcgccag tcaagtaaca accgcgaaaa agttgcgcgg       3200
aggagttgtg tttgtggacg aagtaccgaa aggtcttacc ggaaaactcg       3250
acgcaagaaa aatcagagag atcctcataa aggccaagaa gggcggaaag       3300
tccaaattgt aacacgtgta attctagagc ggccgcttcg agcagacatg       3350
ataagataca ttgatgagtt tggacaaacc acaactagaa tgcagtgaaa       3400
aaaatgcttt atttgtgaaa tttgtgatgc tattgcttta tttgtaacca       3450
ttataagctg caataaacaa gttaacaaca acaattgcat tcattttatg       3500
tttcaggttc aggggaggt gtgggaggtt ttttaaagca agtaaaacct       3550
ctacaaatgt ggtaaaatcg ataagtttaa acagatccag gtggcacttt       3600
tcggggaaat gtgcgcggaa cccctatttg tttatttttc taaatacatt       3650
caaatatgta tccgctcatg agacaataac cctgataaat gcttcaataa       3700
tattgaaaaa ggaagagtat gagtattcaa catttccgtg tcgcccttat       3750
tccctttttt gcggcatttt gccttcctgt ttttgctcac ccagaaacgc       3800
tggtgaaagt aaaagatgct gaagatcagt tgggtgcacg agtgggttac       3850
atcgaactgg atctcaacag cggtaagatc cttgagagtt ttcgccccga       3900
agaacgtttt ccaatgatga gcactttaa agttctgcta tgtggcgcgg        3950
tattatcccg tattgacgcc gggcaagagc aactcggtcg ccgcatacac       4000
tattctcaga atgacttggt tgagtactca ccagtcacag aaaagcatct       4050 tacgatggc atgacagtaa gagaattatg cagtgctgcc ataaccatga       4100
gtgataacac tgcggccaac ttacttctga caacgatcgg aggaccgaag       4150
```

-continued

| | |
|---|---|
| gagctaaccg cttttttgca caacatgggg gatcatgtaa ctcgccttga | 4200 |
| tcgttgggaa ccggagctga atgaagccat accaaacgac gagcgtgaca | 4250 |
| ccacgatgcc tgtagcaatg gcaacaacgt tgcgcaaact attaactggc | 4300 |
| gaactactta ctctagcttc ccggcaacaa ttaatagact ggatggaggc | 4350 |
| ggataaagtt gcaggaccac ttctgcgctc ggcccttccg gctggctggt | 4400 |
| ttattgctga taaatctgga gccggtgagc gtgggtctcg cggtatcatt | 4450 |
| gcagcactgg ggccagatgg taagccctcc cgtatcgtag ttatctacac | 4500 |
| gacggggagt caggcaacta tggatgaacg aaatagacag atcgctgaga | 4550 |
| taggtgcctc actgattaag cattggtaac tgtcagacca agtttactca | 4600 |
| tatatacttt agattgattt aaaacttcat ttttaattta aaaggatcta | 4650 |
| ggtgaagatc ctttttgata atctcatgac caaatccct taacgtgagt | 4700 |
| tttcgttcca ctgagcgtca gaccccgtag aaaagatcaa aggatcttct | 4750 |
| tgagatcctt ttttttctgcg cgtaatctgc tgcttgcaaa caaaaaaacc | 4800 |
| accgctacca gcggtggttt gtttgccgga tcaagagcta ccaactcttt | 4850 |
| ttccgaaggt aactggcttc agcagagcgc agataccaaa tactgtcctt | 4900 |
| ctagtgtagc cgtagttagg ccaccacttc aagaactctg tagcaccgcc | 4950 |
| tacatacctc gctctgctaa tcctgttacc agtggctgct gccagtggcg | 5000 |
| ataagtcgtg tcttaccggg ttggactcaa gacgatagtt accggataag | 5050 |
| gcgcagcggt cgggctgaac ggggggttcg tgcacacagc ccagcttgga | 5100 |
| gcgaacgacc tacaccgaac tgagatacct acagcgtgag ctatgagaaa | 5150 |
| gcgccacgct tcccgaaggg agaaaggcgg acaggtatcc ggtaagcggc | 5200 |
| agggtcggaa caggagagcg cacgagggag cttccagggg gaaacgcctg | 5250 |
| gtatctttat agtcctgtcg ggtttcgcca cctctgactt gagcgtcgat | 5300 |
| ttttgtgatg ctcgtcaggg gggcggagcc tatggaaaaa cgccagcaac | 5350 |
| gcggcctttt tacggttcct ggccttttgc tggccttttg ctcacatggc | 5400 |
| tcgac | 5405 |

<210> SEQ ID NO 2
<211> LENGTH: 5427
<212> TYPE: DNA
<213> ORGANISM: Artificial Sequence
<220> FEATURE:
<223> OTHER INFORMATION: p2luci

<400> SEQUENCE: 2

| | |
|---|---|
| agatcgatct gcgcagcacc atggcctgaa ataacctctg aaagaggaac | 50 |
| ttggttaggt accttctgag gcggaaagaa ccagctgtgg aatgtgtgtc | 100 |
| agttagggtg tggaaagtcc ccaggctccc cagcaggcag aagtatgcaa | 150 |
| agcatgcatc tcaattagtc agcaaccagg tgtggaaagt ccccaggctc | 200 |
| cccagcaggc agaagtatgc aaagcatgca tctcaattag tcagcaacca | 250 |
| tagtcccgcc cctaactccg cccatcccgc cctaactcc gcccagttcc | 300 |
| gcccattctc cgccccatgg ctgactaatt ttttttattt atgcagaggc | 350 |
| cgaggccgcc tcggcctctg agctattcca gaagtagtga ggaggctttt | 400 |
| ttggaggcct aggcttttgc aaaaagcttg attcttctga cacaacagtc | 450 |

-continued

```
tcgaacttaa gctgcagaag ttggtcgtga ggcactgggc aggtaagtat        500
caaggttaca agacaggttt aaggagacca atagaaactg ggcttgtcga        550
gacagagaag actcttgcgt ttctgatagg cacctattgg tcttactgac        600
atccactttg cctttctctc cacaggtgtc cactcccagt tcaattacag        650
ctcttaaggc tagagtactt aatacgactc actataggct agccaccatg        700
acttcgaaag tttatgatcc agaacaaagg aaacggatga taactggtcc        750
gcagtggtgg gccagatgta aacaaatgaa tgttcttgat tcatttatta        800
attattatga ttcagaaaaa catgcagaaa atgctgttat ttttttacat        850
ggtaacgcgg cctcttctta tttatggcga catgttgtgc cacatattga        900
gccagtagcg cggtgtatta taccagacct tattggtatg ggcaaatcag        950
gcaaatctgg taatggttct tataggttac ttgatcatta caaatatctt       1000
actgcatggt ttgaacttct taatttacca aagaagatca tttttgtcgg       1050
ccatgattgg ggtgcttgtt tggcatttca ttatagctat gagcatcaag       1100
ataagatcaa agcaatagtt cacgctgaaa gtgtagtaga tgtgattgaa       1150
tcatgggatg aatggcctga tattgaagaa gatattgcgt tgatcaaatc       1200
tgaagaagga gaaaaaatgg ttttggagaa taacttcttc gtggaaacca       1250
tgttgccatc aaaaatcatg agaaagttag aaccagaaga atttgcagca       1300
tatcttgaac cattcaaaga gaaaggtgaa gttcgtcgtc caacattatc       1350
atggcctcgt gaaatcccgt tagtaaaagg tggtaaacct gacgttgtac       1400
aaattgttag gaattataat gcttatctac gtgcaagtga tgatttacca       1450
aaaatgttta ttgaatcgga cccaggattc ttttccaatg ctattgttga       1500
aggtgccaag aagtttccta atactgaatt tgtcaaagta aaaggtcttc       1550
atttttcgca agaagatgca cctgatgaaa tgggaaaata tatcaaatcg       1600
ttcgttgagc gagttctcaa aaatgaacaa atgtcgacgg gggcccctag       1650
gagatctagc gctggatccc ccggggagct catggaagac gccaaaaaca       1700
taaagaaagg cccggcgcca ttctatcctc tagaggatgg aaccgctgga       1750
gagcaactgc ataaggctat gaagagatac gccctggttc ctggaacaat       1800
tgcttttaca gatgcacata tcgaggtgaa catcacgtac gcggaatact       1850
tcgaaatgtc cgttcggttg gcagaagcta tgaaacgata tgggctgaat       1900
acaaatcaca gaatcgtcgt atgcagtgaa aactctcttc aattctttat       1950
gccggtgttg ggcgcgttat ttatcggagt tgcagttgcg cccgcgaacg       2000
acatttataa tgaacgtgaa ttgctcaaca gtatgaacat ttcgcagcct       2050
accgtagtgt ttgtttccaa aaaggggttg caaaaaattt tgaacgtgca       2100
aaaaaaatta ccaataatcc agaaaattat tatcatggat tctaaaacgg       2150
attaccaggg atttcagtcg atgtacacgt tcgtcacatc tcatctacct       2200
cccggtttta atgaatacga ttttgtacca gagtcctttg atcgtgacaa       2250
aacaattgca ctgataatga attcctctgg atctactggg ttacctaagg       2300
gtgtggccct tccgcataga actgcctgcg tcagattctc gcatgccaga       2350
gatcctattt ttggcaatca aatcattccg gatactgcga ttttaagtgt       2400
```

```
tgttccattc catcacggtt ttggaatgtt tactacactc ggatatttga      2450
tatgtggatt tcgagtcgtc ttaatgtata gatttgaaga agagctgttt      2500
ttacgatccc ttcaggatta caaaattcaa agtgcgttgc tagtaccaac      2550
cctatttcca ttcttcgcca aaagcactct gattgacaaa tacgatttat      2600
ctaatttaca cgaaattgct tctggggggcg caccctctttc gaaagaagtc    2650 ggggaagcgg ttgcaaaacg cttccatctt ccagggatac gacaaggata      2700
tgggctcact gagactacat cagctattct gattacaccc gagggggatg      2750
ataaaccggg cgcggtcggt aaagttgttc cattttttga agcgaaggtt      2800
gtggatctgg ataccgggaa aacgctgggc gttaatcaga gaggcgaatt      2850
atgtgtcaga ggacctatga ttatgtccgg ttatgtaaac aatccggaag      2900
cgaccaacgc cttgattgac aaggatggat ggctacattc tggagacata      2950
gcttactggg acgaagacga acacttcttc atagttgacc gcttgaagtc      3000
tttaattaaa tacaaaggat atcaggtggc ccccgctgaa ttggaatcga      3050
tattgttaca acaccccaac atcttcgacg cgggcgtggc aggtcttccc      3100
gacgatgacg ccggtgaact tcccgccgcc gttgttgttt tggagcacgg      3150
aaagacgatg acggaaaaag agatcgtgga ttacgtcgcc agtcaagtaa      3200
caaccgcgaa aaagttgcgc ggaggagttg tgtttgtgga cgaagtaccg      3250
aaaggtctta ccgaaaaact cgacgcaaga aaaatcagag agatcctcat      3300
aaaggccaag aagggcggaa agtccaaatt gtaacacgtg taattctaga      3350
gcggccgctt cgagcagaca tgataagata cattgatgag tttggacaaa      3400
ccacaactag aatgcagtga aaaaaatgct ttatttgtga aatttgtgat      3450
gctattgctt tatttgtaac cattataagc tgcaataaac aagttaacaa      3500
caacaattgc attcatttta tgtttcaggt tcaggggggag gtgtgggagg      3550 ttttttaaag caagtaaaac ctctacaaat gtggtaaaat cgataagttt      3600
aaacagatcc aggtggcact tttcggggaa atgtgcgcgg aacccctatt      3650
tgtttatttt tctaaataca ttcaaatatg tatccgctca tgagacaata      3700
accctgataa atgcttcaat aatattgaaa aaggaagagt atgagtattc      3750
aacatttccg tgtcgccctt attccctttt ttgcggcatt ttgccttcct      3800
gtttttgctc acccagaaac gctggtgaaa gtaaaagatg ctgaagatca      3850
gttgggtgca cgagtgggtt acatcgaact ggatctcaac agcggtaaga      3900
tccttgagag ttttcgcccc gaagaacgtt ttccaatgat gagcactttt      3950
aaagttctgc tatgtggcgc ggtattatcc cgtattgacg ccgggcaaga      4000
gcaactcggt cgccgcatac actattctca gaatgacttg gttgagtact      4050
caccagtcac agaaaagcat cttacggatg gcatgacagt aagagaatta      4100
tgcagtgctg ccataaccat gagtgataac actgcggcca acttacttct      4150
gacaacgatc ggaggaccga aggagctaac cgcttttttg cacaacatgg      4200
gggatcatgt aactcgcctt gatcgttggg aaccggagct gaatgaagcc      4250
ataccaaacg acgagcgtga caccacgatg cctgtagcaa tggcaacaac      4300
gttgcgcaaa ctattaactg gcgaactact tactctagct tcccggcaac      4350
aattaataga ctggatggag gcggataaag ttgcaggacc acttctgcgc      4400
```

-continued

```
tcggcccttc cggctggctg gtttattgct gataaatctg gagccggtga         4450
gcgtgggtct cgcggtatca ttgcagcact ggggccagat ggtaagccct         4500
cccgtatcgt agttatctac acgacgggga gtcaggcaac tatggatgaa         4550
cgaaatagac agatcgctga gataggtgcc tcactgatta agcattggta         4600
actgtcagac caagtttact catatatact ttagattgat ttaaaacttc         4650
atttttaatt taaaggatc taggtgaaga tccttttga taatctcatg           4700
accaaaatcc cttaacgtga gttttcgttc cactgagcgt cagaccccgt         4750
agaaaagatc aaaggatctt cttgagatcc ttttttctg cgcgtaatct          4800
gctgcttgca acaaaaaaa ccaccgctac agcggtggt ttgtttgccg           4850
gatcaagagc taccaactct ttttccgaag gtaactggct tcagcagagc         4900
gcagatacca aatactgtcc ttctagtgta gccgtagtta ggccaccact         4950
tcaagaactc tgtagcaccg cctacatacc tcgctctgct aatcctgtta         5000
ccagtggctg ctgccagtgg cgataagtcg tgtcttaccg ggttggactc         5050
aagacgatag ttaccggata aggcgcagcg gtcgggctga acggggggtt         5100
cgtgcacaca gcccagcttg gagcgaacga cctacaccga actgagatac         5150
ctacagcgtg agctatgaga aagcgccacg cttcccgaag ggagaaaggc         5200
ggacaggtat ccggtaagcg gcagggtcgg aacaggagag cgcacgaggg         5250
agcttccagg gggaaacgcc tggtatcttt atagtcctgt cgggtttcgc         5300
cacctctgac ttgagcgtcg attttttgtga tgctcgtcag ggggggcggag       5350
cctatggaaa aacgccagca acgcggcctt tttacggttc ctggccttt         5400
gctggccttt tgctcacatg gctcgac                                  5427
```

<210> SEQ ID NO 3
<211> LENGTH: 3705
<212> TYPE: DNA
<213> ORGANISM: Artificial Sequence
<220> FEATURE:
<223> OTHER INFORMATION: pRL-SV40

<400> SEQUENCE: 3

```
agatctgcgc agcaccatgg cctgaaataa cctctgaaag aggaacttgg          50
ttaggtacct tctgaggcgg aaagaaccag ctgtggaatg tgtgtcagtt          100
agggtgtgga aagtccccag gctccccagc aggcagaagt atgcaaagca         150
tgcatctcaa ttagtcagca accaggtgtg gaaagtcccc aggctcccca         200
gcaggcagaa gtatgcaaag catgcatctc aattagtcag caaccatagt         250
cccgcccta actccgccca tcccgcccct aactccgccc agttccgccc           300
attctccgcc ccatggctga ctaatttttt ttatttatgc agaggccgag          350
gccgcctcgg cctctgagct attccagaag tagtgaggag gcttttttgg         400
aggcctaggc ttttgcaaaa agcttgattc ttctgacaca acagtctcga         450
acttaagctg cagaagttgg tcgtgaggca ctgggcaggt aagtatcaag         500
gttacaagac aggtttaagg agaccaatag aaactgggct tgtcgagaca         550
gagaagactc ttgcgtttct gataggcacc tattggtctt actgacatcc         600
actttgcctt tctctccaca ggtgtccact cccagttcaa ttacagctct         650
```

-continued

```
taaggctaga gtacttaata cgactcacta taggctagcc accatgactt      700
cgaaagttta tgatccagaa caaaggaaac ggatgataac tggtccgcag      750
tggtgggcca gatgtaaaca aatgaatgtt cttgattcat ttattaatta      800
ttatgattca gaaaacatg cagaaaatgc tgttattttt ttacatggta       850
acgcggcctc ttcttattta tggcgacatg ttgtgccaca tattgagcca      900
gtagcgcggt gtattatacc agaccttatt ggtatgggca aatcaggcaa      950
atctggtaat ggttcttata ggttacttga tcattacaaa tatcttactg     1000
catggtttga acttcttaat ttaccaaaga agatcatttt tgtcggccat     1050
gattggggtg cttgtttggc atttcattat agctatgagc atcaagataa     1100
gatcaaagca atagttcacg ctgaaagtgt agtagatgtg attgaatcat     1150
gggatgaatg gcctgatatt gaagaagata ttgcgttgat caaatctgaa     1200
gaaggagaaa aaatggtttt ggagaataac ttcttcgtgg aaaccatgtt     1250
gccatcaaaa atcatgagaa agttagaacc agaagaattt gcagcatatc     1300
ttgaaccatt caaagagaaa ggtgaagttc gtcgtccaac attatcatgg     1350
cctcgtgaaa tcccgttagt aaaaggtggt aaacctgacg ttgtacaaat     1400
tgttaggaat tataatgctt atctacgtgc aagtgatgat ttaccaaaaa     1450 tgttttattga atcggaccca ggattctttt ccaatgctat tgttgaaggt    1500
gccaagaagt ttcctaatac tgaatttgtc aaagtaaaag gtcttcattt     1550
ttcgcaagaa gatgcacctg atgaaatggg aaaatatatc aaatcgttcg     1600
ttgagcgagt tctcaaaaat gaacaataat tctagagcgg ccgcttcgag    1650
cagacatgat aagatacatt gatgagtttg acaaaccac aactagaatg      1700 cagtgaaaaa aatgctttat ttgtgaaatt tgtgatgcta ttgctttatt     1750
tgtaaccatt ataagctgca ataaacaagt taacaacaac aattgcattc     1800
attttatgtt tcaggttcag ggggaggtgt gggaggtttt taaaagcaag     1850
taaaacctct acaaatgtgg taaaatcgat aaggatccag gtggcacttt     1900
tcggggaaat gtgcgcggaa cccctatttg tttattttc taaatacatt      1950 caaatatgta tccgctcatg agacaataac cctgataat gcttcaataa      2000 tattgaaaaa ggaagagtat gagtattcaa catttccgtg tcgcccttat     2050 tcccttttt gcggcatttt gccttcctgt ttttgctcac ccagaaacgc      2100
tggtgaaagt aaaagatgct gaagatcagt tgggtgcacg agtgggttac     2150
atcgaactgg atctcaacag cggtaagatc cttgagagtt ttcgccccga    2200
agaacgtttt ccaatgatga gcacttttaa agttctgcta tgtggcgcgg    2250
tattatcccg tattgacgcc gggcaagagc aactcggtcg ccgcatacac     2300
tattctcaga atgacttggt tgagtactca ccagtcacag aaaagcatct     2350
tacggatggc atgacagtaa gagaattatg cagtgctgcc ataaccatga    2400
gtgataacac tgcggccaac ttacttctga caacgatcgg aggaccgaag    2450
gagctaaccg cttttttgca caacatgggg gatcatgtaa ctcgccttga     2500
tcgttgggaa ccggagctga atgaagccat accaaacgac gagcgtgaca    2550
ccacgatgcc tgtagcaatg gcaacaacgt tgcgcaaact attaactggc     2600
gaactactta ctctagcttc ccggcaacaa ttaatagact ggatggaggc     2650
```

```
ggataaagtt gcaggaccac ttctgcgctc ggcccttccg gctggctggt           2700
ttattgctga taaatctgga gccggtgagc gtgggtctcg cggtatcatt           2750
gcagcactgg ggccagatgg taagcccctcc cgtatcgtag ttatctacac          2800
gacggggagt caggcaacta tggatgaacg aaatagacag atcgctgaga           2850
taggtgcctc actgattaag cattggtaac tgtcagacca agtttactca           2900
tatatacttt agattgattt aaaacttcat ttttaattta aaaggatcta           2950
ggtgaagatc cttttgata atctcatgac caaaatccct taacgtgagt            3000
tttcgttcca ctgagcgtca gaccccgtag aaaagatcaa aggatcttct           3050
tgagatcctt ttttctgcg cgtaatctgc tgcttgcaaa caaaaaaacc            3100
accgctacca gcggtggttt gtttgccgga tcaagagcta ccaactcttt           3150
ttccgaaggt aactggcttc agcagagcgc agataccaaa tactgtcctt           3200
ctagtgtagc cgtagttagg ccaccacttc aagaactctg tagcaccgcc           3250
tacatacctc gctctgctaa tcctgttacc agtggctgct gccagtggcg           3300
ataagtcgtg tcttaccggg ttggactcaa gacgatagtt accggataag           3350
gcgcagcggt cgggctgaac ggggggttcg tgcacacagc ccagcttgga           3400
gcgaacgacc tacaccgaac tgagatacct acagcgtgag ctatgagaaa           3450
gcgccacgct tcccgaaggg agaaaggcgg acaggtatcc ggtaagcggc           3500
agggtcggaa caggagagcg cacgagggag cttccagggg gaaacgcctg           3550
gtatctttat agtcctgtcg ggtttcgcca cctctgactt gagcgtcgat           3600
ttttgtgatg ctcgtcaggg gggcggagcc tatggaaaaa cgccagcaac           3650
gcggcctttt tacggttcct ggccttttgc tggccttttg ctcacatggc           3700
tcgac                                                            3705

<210> SEQ ID NO 4
<211> LENGTH: 52
<212> TYPE: DNA
<213> ORGANISM: Artificial Sequence
<220> FEATURE:
<223> OTHER INFORMATION: Primer lucR

<400> SEQUENCE: 4
ggaagatctg tttaaacgga tccgtcgaca tttgttcatt tttgagaact cg        52

<210> SEQ ID NO 5
<211> LENGTH: 20
<212> TYPE: DNA
<213> ORGANISM: Artificial Sequence
<220> FEATURE:
<223> OTHER INFORMATION: Primer Xcm

<400> SEQUENCE: 5
ggtgaagttc gtcgtccaac                                            20

<210> SEQ ID NO 6
<211> LENGTH: 80
<212> TYPE: DNA
<213> ORGANISM: Artificial Sequence
<220> FEATURE:
<223> OTHER INFORMATION: Primer 2lucA1

<400> SEQUENCE: 6
```

-continued aaatcagaga gatcctcata aaggccaaga agggcggaaa gtccaaattg      50
taacacgtgt aattctagag cggccgcttc      80

<210> SEQ ID NO 7
<211> LENGTH: 31
<212> TYPE: DNA
<213> ORGANISM: Artificial Sequence
<220> FEATURE:
<223> OTHER INFORMATION: Primer 2lucA2

<400> SEQUENCE: 7
gaccgtttaa acttatcgat tccacatttg t      31

<210> SEQ ID NO 8
<211> LENGTH: 82
<212> TYPE: DNA
<213> ORGANISM: Artificial Sequence
<220> FEATURE:
<223> OTHER INFORMATION: Oligonucleotide luci1

<400> SEQUENCE: 8
tcgacggggg ccctaggag atctagcgct ggatccccg gggagctcau      50 ggaagacgcc aaaaacataa agaaaggccc gg      82

<210> SEQ ID NO 9
<211> LENGTH: 80
<212> TYPE: DNA
<213> ORGANISM: Artificial Sequence
<220> FEATURE:
<223> OTHER INFORMATION: Oligonucleotide luci2

<400> SEQUENCE: 9
cgccgggcct ttctttatgt ttttggcgtc ttccatgagc tccccggggg      50
atccagcgct agatctccta ggggcccccg      80

<210> SEQ ID NO 10
<211> LENGTH: 33
<212> TYPE: DNA
<213> ORGANISM: Artificial Sequence
<220> FEATURE:
<223> OTHER INFORMATION: Primer SAA2luc

<400> SEQUENCE: 10
ccatgtcgac gggggcccct aggaaaaaagg gct      33

<210> SEQ ID NO 11
<211> LENGTH: 34
<212> TYPE: DNA
<213> ORGANISM: Artificial Sequence
<220> FEATURE:
<223> OTHER INFORMATION: Primer BglP1

<400> SEQUENCE: 11
gttcgaagag atcttccctt aagaagttag cctg      34

<210> SEQ ID NO 12
<211> LENGTH: 75
<212> TYPE: DNA
<213> ORGANISM: Artificial Sequence
<220> FEATURE:
<223> OTHER INFORMATION: Oligonucleotide for cloning of mouse mammary
      tumor virus recoding sequence.

<400> SEQUENCE: 12

```
gtcgacagct gaaaattcaa aaaacttgta aaggggcagt cccctagccc          50
cactcaaaag ggggataagg gatcc                                    75

<210> SEQ ID NO 13
<211> LENGTH: 76
<212> TYPE: DNA
<213> ORGANISM: Artificial Sequence
<220> FEATURE:
<223> OTHER INFORMATION: Oligonucleotide for cloning of mouse mammary
      tumor virus control sequence.

<400> SEQUENCE: 13
gtcgacagct gaaaattcga agaagcttgt aaaggggcag tcccctagcc          50
ccactcaaaa gggggataaa ggatcc                                   76

<210> SEQ ID NO 14
<211> LENGTH: 88
<212> TYPE: DNA
<213> ORGANISM: Artificial Sequence
<220> FEATURE:
<223> OTHER INFORMATION: Oligonucleotide for cloning of Moloney murine
      leukemia virus recoding sequence.

<400> SEQUENCE: 14
gtcgacgacc ctagatgact agggaggtca gggtcaggag ccccccctg           50 aacccaggat aaccctcaaa gtcgggggc aaggatcc                        88

<210> SEQ ID NO 15
<211> LENGTH: 88
<212> TYPE: DNA
<213> ORGANISM: Artificial Sequence
<220> FEATURE:
<223> OTHER INFORMATION: Oligonucleotide for cloning of Moloney murine
      leukemia virus control sequence.

<400> SEQUENCE: 15
gtcgacgacc ctagatgacc agggaggtca gggtcaggag ccccccctg           50 aacccaggat aaccctcaaa gtcgggggc aaggatcc                        88

<210> SEQ ID NO 16
<211> LENGTH: 30
<212> TYPE: DNA
<213> ORGANISM: Artificial Sequence
<220> FEATURE:
<223> OTHER INFORMATION: Primer B1Gpr

<400> SEQUENCE: 16
gcagggatcc ctttagttgc cccctatct                                30

<210> SEQ ID NO 17
<211> LENGTH: 31
<212> TYPE: DNA
<213> ORGANISM: Artificial Sequence
<220> FEATURE:
<223> OTHER INFORMATION: Primer fsAZ1

<400> SEQUENCE: 17
ggccgtcgac tagggttgcc cttcattgct g                             31

<210> SEQ ID NO 18
<211> LENGTH: 31
<212> TYPE: DNA
<213> ORGANISM: Artificial Sequence
<220> FEATURE:
```

-continued

<223> OTHER INFORMATION: Primer fsAZ2

<400> SEQUENCE: 18
ggccggatcc actgtgatcc cgctgactgt t                            31